United States Patent [19]

Sharma et al.

[11] Patent Number: 5,130,297

[45] Date of Patent: Jul. 14, 1992

[54] CONJUGATES USEFUL IN AMELIORATING AUTOIMMUNITY MHC-II-PEPTIDE

[75] Inventors: Somesh D. Sharma, Los Altos; L. Bernard Lerch, Menlo Park; Brian R Clark, Redwood City, all of Calif.

[73] Assignee: Anergen, Inc., Redwood City, Calif.

[21] Appl. No.: 576,084

[22] Filed: Aug. 30, 1990

Related U.S. Application Data

[63] Continuation of Ser. No. 210,594, Jun. 23, 1988, abandoned.

[51] Int. Cl.$^5$ ...................... A61K 35/28; A61K 37/02
[52] U.S. Cl. ........................................ 514/8; 514/825; 514/903; 530/395; 530/403; 530/838
[58] Field of Search ............... 530/395, 402, 403, 838; 514/8, 825, 903

[56] References Cited

U.S. PATENT DOCUMENTS

| | | | |
|---|---|---|---|
| 4,199,565 | 4/1980 | Fullerton | 424/89 |
| 4,400,376 | 8/1983 | Sanderson | 424/88 |
| 4,478,823 | 10/1984 | Sanderson | 424/88 |
| 4,762,915 | 8/1988 | Kung | 530/405 |

OTHER PUBLICATIONS

*Fundamental Immunology*, W. E. Paul (ed), 1989, pp. 69-73.
Cooperman, in *Ribosomes* (University Park Press, Baltimore), pp. 531-554 (1980).
Hall et al., *Biochemistry* 24:5702-5711 (1985).
Wraith et al., *Cell* 59:247-255 (1989).
Luescher et al., *J. Biol. Chem.* 265:11177-11184 (1990).
Rennie et al., *Lancet* (10 Dec. 1983) pp. 1338-1340.
Diener et al., *Science* (1986) 231:148-150.
Sterz et al., *J. Immunol.* (1985) 134:841-846.
Killen et al., *J. Immunol.* (1984) 133:2549-2553.
Hixson *Med. Tribune* (28 Jan. 1985) pp. 4-5.
Liu et al., *Science* (1989) 239:395-397.
Shizuru et al., *Science* (1988) 240:659-662.
Watts et al., *Proc. Natl. Acad. Sci. USA* (1984) 81:7564-7568.

Clemetson et al., *Membrane Proteins: A Laboratory Manual* (1986) A. Azzi et al., editors, pp. 57-64.
Harcourt et al., *Immunol. Today* (1987) 8(11):(news and features section).
Watts et al., *Processing and Presentation of Antigens* (1988) Academic Press, New York, pp. 143-155.
Sriram et al., *Concepts Immunolpathol.* (1987) 4:275-286.
Turkewitz et al., *Molecular Immunol.* (1983) 20(11):1139-1147.
Sekaly et al., *J. Exp. Med.* (1986) 164:1490-1504.
Puri et al., *Eur. J. Immunol.* (1980) 10:273-281.
Marx et al., *Science* (1987) 238:613-614.
Marrack et al., *Nature* (1988) 332:840-842.
Townsend et al., *Nature* (1987) 329:482-483.
Springer et al., *Proc. Natl. Acad. Sci. USA* (1976) 73(7):2481-2485.
Bjorkman et al., *Nature* (1987) 329:512-518.
Bjorkman et al., *Nature* (1987) 329:504-512.
Guillet et al., *Science* (1987) 235:865-870.

(List continued on next page.)

*Primary Examiner*—Christine Nucker
*Assistant Examiner*—T. Cunningham
*Attorney, Agent, or Firm*—Townsend and Townsend

[57] ABSTRACT

The invention is directed to methods and materials useful in treating autoimmune diseases. The therapeutic agents are of the formula $X\overset{1}{-}MHC\overset{2}{-}peptide$ or $MHC\overset{1}{-}peptide\overset{2}{-}X$ wherein X represents a functional moiety selected from a toxin and a labeling group; MHC is an effective portion of the MHC glycoprotein, said glycoprotein dissociated from the cell surface on which it normally resides; and "peptide" represents an antigenic peptide sequence associated with an autoantigen; $\underline{1}$ represents a covalent bond or a linker bound to X and MHC or to X and peptide by covalent bonds; and $\underline{2}$ represents a covalent bond, to noncovalent association, or a linker covalently bound to or associated with the MHC and peptide. These complexes can be used to target helper T-cells which are specifically immunoreactive with autoantigens.

4 Claims, 9 Drawing Sheets

OTHER PUBLICATIONS

Nakanishi et al., *Mol. Immunol.* (1983) 20(11):1227–1231.

Babbitt et al., *Nature* (1985) 317:359–361.

Watts et al., *Proc. Natl. Acad. Sci. USA* (1985) 82:5480–5484.

Unanue et al., *Science* (1987) 236:551–557.

Buus et al., *Science* (1987) 235:1353–1358.

Vitetta et al., *Science* (1987) 238:1098–1104.

Pastan et al., *Cell* (1986) 47:641–648.

Estess et al., "Regulation of Immune Gene Expression" Feldman et al., editors, The Humana Press, Inc., (1985, pp. 3–19).

D. H. Margules, et al. *Immunol. Res.* G:101–116 (1987), Engineering Soluble MHC molecules: how & why.

Ceredig et al., "High Antigen Concentration ... ", *Eur. J. Immunol.*, 1986, 16:30–34.

Essery et al., "Interleukin-2 Can Prevent and Reverse ... ", *Immunology*, 1988, 64:413–417.

Jenkins et al., "Antigen Presentation by Chemically ... ", *J. Exper. Med.*, 1987, 165:302–319.

Klein, "What Causes Immunological Nonresponsiveness?", *Immun. Reviews*, 1984, 81.

Lamb et al., "Induction of Tolerance in Influenza ... ", *J. Exp. Med.*, 1983, 157:1434–1447.

Lamb et al., "Essential Requirement for Major Histocompatibility ... ", *Nature*, 1984, 308.

Lamb et al., "Influence of Antigen Structure ... ", *Immunology*, 1986, 57:331–335.

Lamb et al., "Antigen-Specified T Cell Unresponsiveness ... ," *Eur. J. Immunol.*, 1987, 17:1641–1644.

Larche et al., "A Novel T-Lymphocyte Molecule ... ," *Immunol.*, 1988 64:101–105.

Madsen et al., "Immunological Unresponsiveness ... ," *Nature*, 1988, 332.

Miller et al., "The Induction of Cell-Mediated ... ," *J. Exp. Med.*, 1979, 149:758–773.

Nau et al., "Inhibition of IL 2-Driven Proliferation ... ," *J. Immun.*, 1987, 139:114–122.

Quill et al., "Stimulation of Normal Inducer T Cell Clones ... ," *J. Immun.*, 1987, 138:3704–3712.

Suzuki et al., "Antigen-Induced Suppression ... ," *J. Immun.*, 1988.

Zanders et al., "Tolerance of T-Cell Clones ... ," *Nature*, 1983, 303.

Zanders et al., "Biochemical Events Initiated by Exposure ... ", *Eur. J. Immunol.*, 1985, 13:302–305.

Germain, "Accessory Cell Stimulation ... ," *J. Immun.*, 1981, 127.

```
                                100                                110
Asp Gly Asp Phe Ala Ile Val His Met Thr Lys Leu Leu Asp Tyr Thr Gly
GAU GGU GAU UUU GCC AUU GUU CAC AUG ACC AAA CUG CUU GAU UAU ACG GGA
            300                     320                     340

120                          130              150
Lys Ile Met Trp Thr Pro Pro Ala Ile Phe Lys Ser Tyr Gyx Glu Ile Val
AAA AUA AUG UGG ACA CCA CCU GCA AUC UUC AAA AGC UAU UGU GAA AUU GUA
            360                     380

140                          160
Thr His Phe Pro Phe Asp Gln Asn Cys Thr Met Lys Leu Gly Ile Trp Thr
ACA CAU UUC CCA UUU GAU CAA AAU UGC ACU AUG AAG UUG GGA AUC UGG ACG
        400                     420                     440

Tyr Asp Gly Thr Lys Val Ser Ile Ser Pro Glu Ser Asp Arg Pro Asp Leu Ser
UAC GAU GGG ACA AAA GUU UCC AUA UCC CCG GAA AGU GAC CGU CCG GAU CUG AGU
        460                     480                     500

170                                180
Thr Phe Met Glu Ser Gly Glu Trp Val Met Lys Asp Tyr Arg Gly Trp Lys His
ACA UUU AUG GAA AGU GGA GAG UGG GUA AUG AAA GAU UAU CGU GGA UGG AAG CAC
        520                     540

190                          200
Trp Val Tyr Tyr Thr Cys Cys Pro Asp Thr Pro Tyr Leu Asp Ile Thr Tyr His
UGG GUG UAU UAU ACC UGC UGU CCU GAC ACU CCU UAC CUG GAU AUC ACC UAC CAU
560                     580                     600
```

```
                                    210                      220
Phe Ile Met Gln Arg Ile Pro Leu Tyr Phe Val Val Asn Val Ile Pro Cys
UUU AUC AUG CAG CGU AUU CCU CUU UAU UUU GUU GUG AAU GUC AUC CCU UGU
            620                 640                 660

Leu Phe Ser Phe Leu Thr Gly Leu Val Phe Tyr Leu Pro Thr Asp Ser Gly
CUG UUU UCA UUU UUA ACU GGA UUA GUA UUU UAC UUA CCA ACU GAU UCA GGU
            680                 700                 720
                                    250
Glu Lys Met Thr Leu Ser Ile Ser Val Leu Leu Ser Leu Thr Val Phe Leu Leu
GAG AAG AUG ACU UUG AGU AUC UCC GUU UUG CUG ACU GUG UUC CUU CUG
            740                 760
        260                                 270
Val Ile Val Glu Leu Ile Pro Ser Thr Ser Ser Ala Val Pro Leu Ile Gly Lys
GUU AUU GUU GAG CUG AUC CCC UCA ACU AGC GCU GUG CCU UUG AUU GGC AAA
            780                 800                 820
                            280                     290
Tyr Met Leu Phe Thr Met Ile Phe Val Ile Ser Ser Ile Ile Thr Val Val
UAC AUG CUU UUU ACA AUG AUU GUC AUC AGU UCA AUC AUC ACU GUU GUU
            840                 860                 880
                    300                         310
Val Ile Asn Thr His Arg Ser Pro Ser Thr His Thr Met Pro Gln Trp Val
GUA AUU AAU ACU CAC CGC UCU CCA AGU ACA CAU ACA AUG CCA CAA UGG GUA
            900                 920
```

FIG. 6-3

```
                                                          330
Arg Lys Ile Phe Ile Asp Thr Ile Pro Asn Val Met Phe Phe Ser Thr Met Lys
CGA AAG AUC UUU AUU GAU ACU AUA CCC AAU GUU AUG UUU UCA ACA AUG AAA
940                         320                         980
                                                                      1,040
                            340
Arg Ala Ser Lys Glu Lys Gln Glu Asn Lys Ile Phe Ala Asp Asp Ile Asp Ile
CGA GCU UCU AAG GAA AAG CAA GAA AAU AAG AUA UUU GCU GAU GAC AUU GAU AUC
    1,000                        1,020
                                                360
Ser Asp Ile Ser Gly Lys Gln Val Thr Gly Glu Val Ile Phe Gln Thr Pro Leu
UCU GAC AUU UCU GGA AAG CAA GUG ACA GGA GAA GUA AUU UUU CAA ACA CCU CUC
              1,060                             1,080
      370
Ile Lys Asn Pro Asp Val Lys Ser Ala Ile Glu Gly Val Lys Tyr Ile Ala Glu
AUU AAA AAU CCA GAU GUC AAA AGU GCU AUU GAG GGA GUC AAA UAU AUU GCA GAG
1,100                        1,120                  380
                                                    1,140
                                390
His Met Lys Ser Asp Glu Ser Asn Ala Ala Glu Glu Trp Lys Tyr Val
CAC AUG AAG UCU GAU GAG GAA UCA AGC AAU GCA GCA GAG GAA UGG AAA UAU GUU
        1,160                       1,180                      400
                                                                  1,200
                    410
Ala Met Val Ile Asp His Ile Leu Leu Cys Val Phe Met Leu Ile Cys Ile Ile
GCA AUG GUG AUU GAU CAC AUU CUG CUG UGU GUC UUC AUG CUG AUU UGU AUA AUU
              1,220                        1,240
                                                                     1,260
                                        430                           420
Gly Thr Val Ser Val Phe Ala Gly Arg Leu Ile Glu Leu Ser Gln Gly Gly
GGU ACA GUU AGC GUG GCU UUU GCU CGU CUC AUU GAA CUC AGU CAA GAG GGC UAA
                         1,280                       1,300
```

```
                                                        His-Gly
              (-)
N-Ac-Ala-Ser-Ala-Gln-Lys-Arg-Pro-Ser-Gln-Arg-Ser-Lys-Tyr-Leu-Ala-
                                10

Thr                                                  Gly
Ser-Ala-Ser-Thr-Met-Asp-His-Ala-Arg-His-Gly-Phe-Leu-Pro-Arg-His-
                 20                                30

Ile                                 Gly
Arg-Asp-Thr-Gly-Ile-Leu-Asp-Ser-Leu-Gly-Arg-Phe-Phe-Gly-Ser-Asp-
                            40

Ser
Arg-Gly-Ala-Pro-Lys-Arg-Gly-Ser-Gly-Lys-Asp-Gly-His-His-Ala-Ala-Arg-
                50                                         60

Ala                   Ser (-)              Thr
Thr-Thr-His-Tyr-Gly-Ser-Leu-Pro-Gln-Lys-Ala-Gln-Gly-His-Arg-Pro-Gln-
                       70                                        80

Met
Asp-Glu-Asn-Pro-Val-Val-His-Phe-Phe-Lys-Asn-Ile-Val-Thr-Pro-Arg-Thr-
                                       90

Pro-Pro-Ser-Gln-Gly-Lys-Gly-Arg-Gly-Leu-Ser-Leu-Ser-Arg-Phe-Ser-
              100                                         110

Arg
Trp-Gly-Ala-Glu-Gly-Gln-Lys-Pro-Gly-Phe-Gly-Tyr-Gly-Gly-Arg-Ala-Ser-
                           120                                    130

Phe              Val
Asp-Tyr-Lys-Ser-Ala-His-Lys-Gly-Leu-Lys-Gly-His-Asp-Ala-Gln-Gly-Thr-
                                     140

Leu-Ser-Lys-Ile-Phe-Lys-Leu-Gly-Gly-Arg-Asp-Ser-Arg-Ser-Gly-Ser-Pro-
                150                                          160

Met-Ala-Arg-Arg-COOH
         170
```

CONJUGATES USEFUL IN AMELIORATING AUTOIMMUNITY MHC-II-PEPTIDE

This is a Continuation of application Ser. No. 07/210,594, filed Jun. 23, 1988, now abandoned.

TECHNICAL FIELD

The invention relates to the treatment of autoimmune diseases and to materials and methods useful in therapy and diagnosis of such diseases. In particular, it concerns complexes which target helper T-cells by using a complex of the major histocompatibility complex (MHC) glycoproteins with peptides representing fragments of antigens associated with autoimmunity. These complexes can be further conjugated to radioisotopes or other labels for diagnostic purposes, or to toxins or other substances which render the complexes therapeutically useful.

BACKGROUND ART

More than 30 autoimmune diseases are presently known; these include many which have received much public attention, including myasthenia gravis (MG) and multiple sclerosis (MS). Characteristic of these diseases is the attack by the immune system on the tissues of the victim—these tissue antigens being resistant in non-diseased individuals because of their recognition by the immune system as "self". In autoimmune diseases, this recognition apparently does not occur, and the tissue of the afflicted subject is treated as an invader—i.e., the immune system sets about destroying this presumed foreign target.

A crude approach to treating autoimmune disease is, of course, general immunosuppression. This has the obvious disadvantage of crippling the ability of the subject to respond to real foreign materials to which it needs to mount an immune response. An only slightly more sophisticated approach relies on the removal of antibodies or immune complexes involving the target tissue. This also has adverse side effects, and is difficult to accomplish. The invention approach, described in detail below, relies on a "clonotypic" reagent—i.e., a reagent which attacks only the cells of the immune system which are responsive to the autoantigen.

In the general paradigm now considered to describe the immune response, specific antigens presented result in a clonal expansion, as first proposed by Burnet in 1959. According to this scenario, a particular subject will have hundreds of thousands of T and B cells each bearing receptors that bind to different antigenic determinants. Upon exposure to an antigen, the antigen selectively binds to cells bearing the appropriate receptors for the antigenic determinants it contains, ignoring the others. The binding results in a cloned population of thousands of daughter cells, each of which is marked by the same receptor. A clonotypic reagent affects only a subset of the T and B cells which are appropriate for the antigen of interest. In the case of the invention compositions, the antigenic determinant is usually that associated with an autoimmune disease.

The clonotypic reagent compositions of the invention are specifically designed to target T-helper cells which represent the clones specific for the antigenic determinant(s) of the tissue which is affected by the autoimmune disease. T-helper cells recognize a determinant only in association with an MHC protein; the complexes of the invention therefore include an effective portion of the MHC protein.

There have, recently, been some related approaches which attempt to interdict the immune response to specific antigens. For example, the autoantigen thyroglobulin has been conjugated to ricin A and the conjugate was shown to suppress specifically the in vitro antibody response of lymphocytes which normally respond to this antigen. It was suggested that such immunotoxins would specifically delete autoantibody-secreting lymphocyte clones (Rennie, D. P., et al, Lancet (Dec. 10, 1983) 1338-1339). Diener, E., et al, Science (1986) 231:148-150 suggested the construction of compounds which cause antigen-specific suppression of lymphocyte function by conjugating daunomycin to the hapten (in this case, of ovalbumin) using an acid-sensitive spacer. The conjugate caused hapten-specific inhibition of antibody secretion by B lymphocytes in vitro and in vivo. A conjugate of daunomycin (with an acid-sensitive spacer) to a monoclonal antibody-specific to T-cells also eliminated the response by T-lymphocytes to concanavalin A. Steerz, R. K. M., et al, J Immunol (1985) 134:841-846 utilized radiation as the toxic element in a toxin conjugate. Rats were administered a radioactively labeled, purified receptor from electric fish, prior to injection with cold receptor. Injection with this receptor is a standard procedure to induce experimental autoimmune myasthenia gravis (EAMG). Control rats that received preinjection only either of cold receptor or radiolabeled albumin, prior to administration of receptor to induce the disease develop the symptoms of EAMG; those pretreated with radioactively-labeled receptor showed reduced symptoms. It was surmised that the labeled, and therefore destructive, receptor selectively eliminated immunocompetent cells. Similar work utilizing a ricin/receptor conjugate for pretreatment was reported by Killen, J. A., et al, J Immunol (1984) 133:2549-2553.

A less specific approach which results in the destruction of T-cells in general is treatment with an IL-2/toxin conjugate as reported by Hixson, J. R., Medical Tribune (Jan. 28, 1985) 4-5. In a converse, but related, approach Liu, M. A., et al, Science (1988) 239:395-397, report a method to "link up" cytotoxic T-cells with a desired target, regardless of the cytotoxic T-cell specificity. In this approach, antibody specific to the universal cytotoxic T-lymphocyte receptor CD3 was conjugated to a hormone specific for a surface receptor on the target tumor cell. The conjugate was capable of activating cytotoxic T-lymphocytes to destroy human melanoma cells when melanocyte-stimulating hormone was the hormone used.

The invention compositions and methods are designed to target helper T-cells which recognize a particular antigen in association with a glycoprotein encoded by the major histocompatibility complex (MHC). The current model of immunity postulates that antigens mobilize an immune response, at least in part, by being ingested by an antigen-presenting cell (APC) which contains on its surface a Class II glycoprotein encoded by a gene in the MHC. The antigen is then presented to a specific T helper cell in the context of the surface-bound MHC glycoprotein, and by interaction of the antigen-specific T-cell receptor with this antigen-glycoprotein complex, the T helper cell is stimulated to mediate the antigen-specific immune response, including induction of cytotoxic T-cell function, induction of B cell function, and secretion of a number of factors aiding and abetting this response.

The involvement of the MHC Class II proteins in autoimmune disease has been shown in animal models. Administration of antibodies to either MHC Class II proteins themselves or antibodies to agents that induce expression of the MHC Class II genes interferes with development of the autoimmune condition in these model systems. The role of helper T-cells has also been demonstrated in these models by counteracting the autoimmune system using anti-CD4 monoclonal antibodies; CD4 is the characteristic helper T-cell receptor (Shizuru, J. A. et al, *Science* (1988) 240:659–662).

The invention complexes effectively substitute for the antigen-presenting cell in evoking the interaction of the T-lymphocytes and other cells of the immune system with respect to the antigen. It has been shown that isolated MHC Class II antigen in and of itself can effectively replace the antigen-presenting cell in the presentation of antigen epitopes to a T-helper lymphocyte (Watts, T. H., et al, *Proc Natl Acad Sci USA* (1984) 81:7564–7568. However, by substituting an effector function, such as a toxin, for the antigen presenting cell (APC) surface, the antigen is made effective in destroying the immune response it would otherwise create; by substituting a label for the APC surface, the antigen is caused to identify the portions of the immune system with which it interacts.

DISCLOSURE OF THE INVENTION

The invention is directed to methods to identify and destroy those aspects of the immune system which are responsible for undesirable autoimmunity. The invention provides forms of an autoantigen which interact with the immune system, in a manner analogous to those initiated by the autoantigen itself to cause the autoimmune reaction, but with modifications to provide additional functions, for example, those which permit identification of the relevant portions of the immune system, and, more importantly, others which destroy the capacity of the immune system to respond in this undesirable manner.

The invention compositions are three component complexes of 1) an effective portion of the MHC-encoded antigen-presenting glycoprotein; 2) an effective portion of the antigen; and 3) an effector. The first two components, which may be bound covalently or by noncovalent association, are in turn conjugated to the third, effector, component, most commonly a toxin or a label. The effector component, substitutes for the APC surface, and alters the effect of the complex with regard to the immune system target.

Thus, in one aspect, the invention is directed to compositions of matter which are the above-described complexes. In other aspects, the invention is directed to pharmaceutical compositions wherein the complexes of the invention are active ingredients, to methods of down-regulating the immune system with regard to a particular antigen, especially a self-antigen, and to methods to identify portions of the immune system reactive with a specific antigen, using the complexes and pharmaceutical compositions of the invention.

BRIEF DESCRIPTION OF THE DRAWINGS

FIG. 6 shows the amino acid sequence and encoding mRNA for the alpha subunit of acetylcholine receptor protein.

FIG. 7 shows the amino acid sequence of myelin basic protein.

MODES OF CARRYING OUT THE INVENTION

The invention complexes contain three components: a peptide which represents an autoantigen or other antigenic sequence with relevant effect on the immune system; an effective portion of the MHC-encoded glycoprotein involved in antigen presentation; and an effector component which is generally a toxin or a label. In general, the effector portion is covalently conjugated to the MHC-encoded glycoprotein or, in some cases, to the antigen; the association between the peptide antigen and the MHC protein·can be by covalent or by noncovalent bonding. Each of the components of the system is described separately below; followed by description of the methods by which these complexes can be prepared, evaluated and employed.

The MHC-Derived Component

The glycoproteins encoded by the MHC have been extensively studied in both the human and murine systems. In general, they have been classified as Class I glycoproteins, found on the surfaces of all cells and primarily recognized by cytotoxic T-cells; and Class II which are found on the surfaces of several cells, including accessory cells such as macrophages, and are involved in presentation of antigens to helper T-cells. Some of the histocompatibility proteins have been isolated and characterized.

Methods for purifying the murine I-A (Class II) histocompatibility proteins have been disclosed by Turkewitz, A. P., et al, *Molecular Immunology* (1983) 20:1139–1147. The isolated antigens encoded by the I-A and I-E subregions were shown to consist of two non-covalently bonded peptide chains: an alpha chain of 32-38 kd and a beta chain of 26-29 kd. A third, invariant, 31 kd peptide is noncovalently associated with these two peptides, but it is not polymorphic and does not appear to be a component of the antigens on the cell surface (Sekaly, R. P., *J Exp Med* (1986) 164:1490-1504). The alpha and beta chains of seven allelic variants of the I-A region have been cloned and sequenced (Estess, "T-cell Clones", 3-19).

The human Class I proteins have also been studied. The MHC of humans (HLA) on chromosome 6 has three loci, HLA-A, HLA-B, and HLA-C, the first two of which have a large number of alleles encoding alloantigens. These are found to consist of a 44 kd subunit and a 12 kd beta$_2$-microglobulin subunit which is common to all antigenic specificities. Isolation of these detergent-soluble HLA antigens was described by Springer, T. A., et al, *Proc Natl Acad Sci USA* (1976) 73:2481–2485; Clementson, K. J., et al, in "Membrane Proteins" Azzi, A., ed; Bjorkman, P., Ph.D. Thesis Harvard (1984).

Figure 2A:
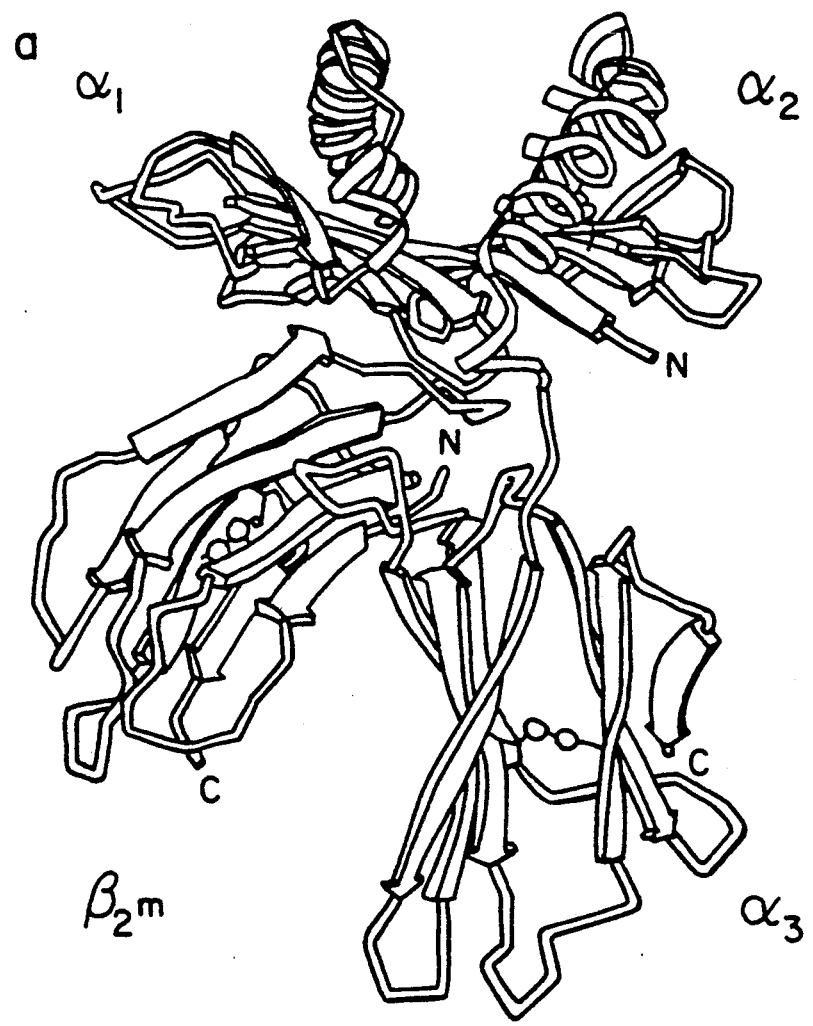
FIG. 2 is a diagram of a typical complex of the invention.
Figure 2B:
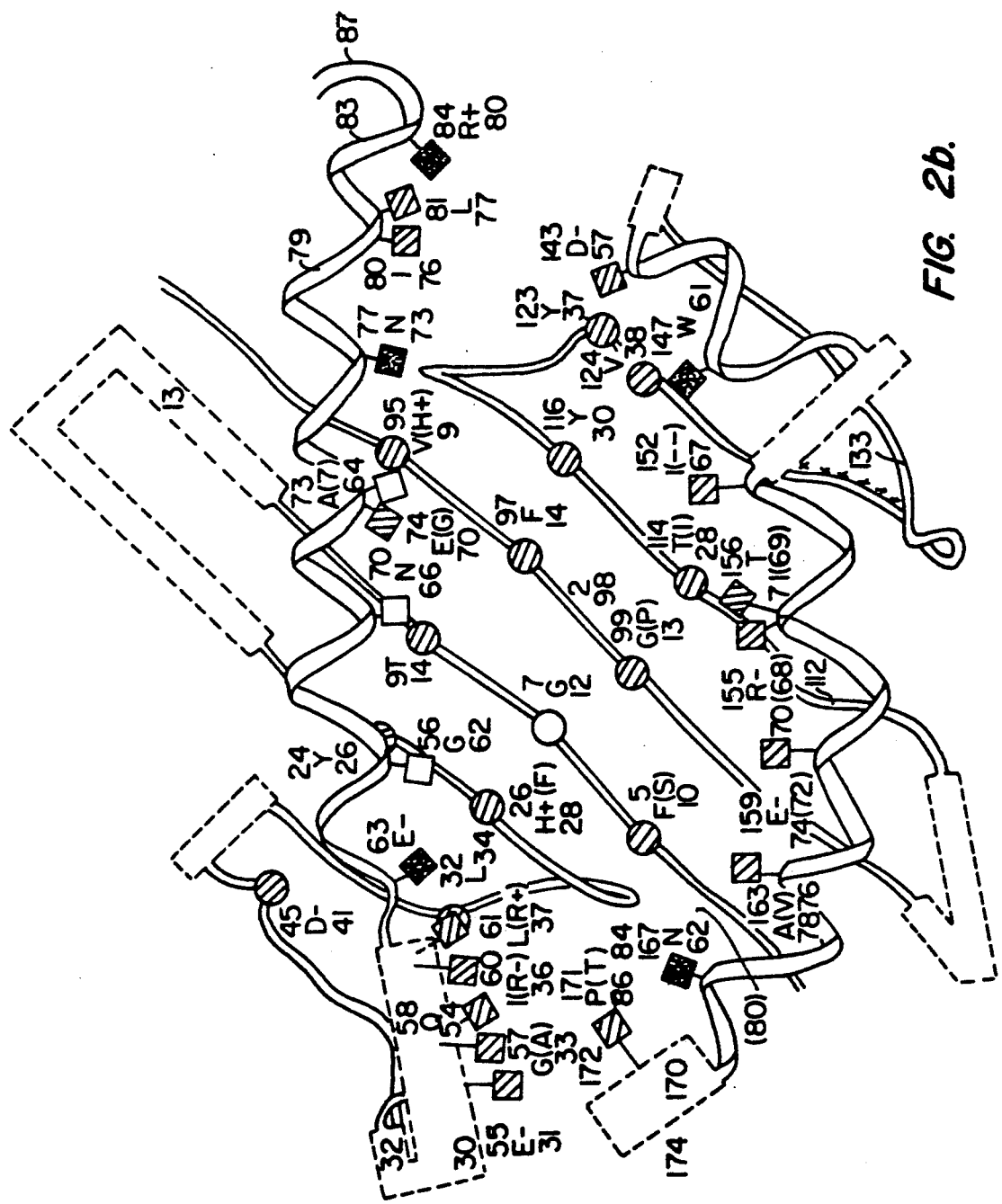
Figure 5:
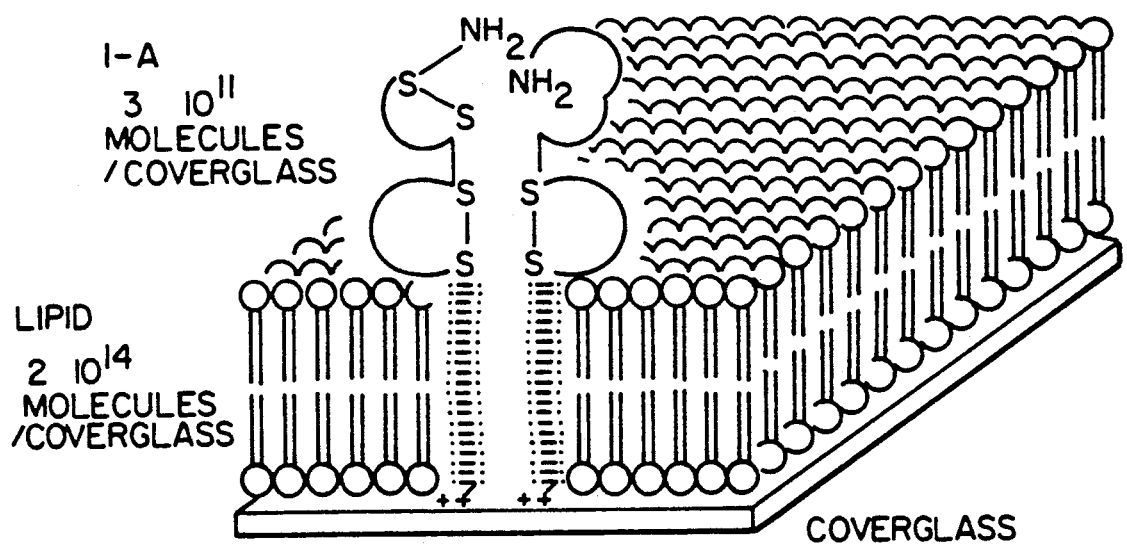
FIG. 5 is a diagram of a planar membrane bilayer including the MHC glycoprotein, mimicking the surface of the antigen presenting cell.

Further work has resulted in a detailed picture of the 3-D structure of HLA-A2, a Class I human antigen. (Bjorkman, P. J., et al, *Nature* (1987) 329:506–512, 512–518). In this picture, the beta2-microglobulin protein and alpha3 segment of the heavy chain are associated; the alpha1 and alpha2 regions of the heavy chain appear to form the base of the antigen-binding pocket (*Science* (1987) 238:613–614) Bjorkman, P. J. et al *Nature* (supra). Soluble HLA-A2 can be purified after papain digestion of plasma membranes from the homozygous human lymphoblastoid cell line J-Y as described by Turner, M. J. et al, *J Biol Chem* (1975) 250:4512–4519; Parham P., et al, *J Biol Chem* (1977) 252:7555–7567. Papain cleaves the 44 kd chain close to the transmembrane region yielding a molecule comprised of alpha$_1$, alpha$_2$, alpha$_3$ and beta$_2$ microglobulin A representation of the deduced three dimensional structure of the Class I HLA-A2 antigen is shown in FIG. 2.

While the three dimensional structure of Class II MHC antigens is not known in such detail, it is thought that Class II glycloproteins have a domain structure similar to that of Class I. It is formed from the N-terminal domain portions of two Class II chains which extend from the membrane bilayer. The N-terminal portion of one chain has two domains of homology with the alpha$_1$ and alpha$_2$ regions of the MHC Class I antigen sequence. The opposing chain contains two domains designated beta$_1$ and beta$_2$. Cloning of the Class II antigen genes (as described by Estess supra) permits manipulation of the Class II MHC binding domains for example, as described below.

The MHC glycoprotein portion of the complexes of the invention, then, can be obtained by isolation from lymphocytes and screened for the ability to bind the desired peptide antigen. MHC glycoproteins have been isolated from a multiplicity of cells using a variety of techniques including solubilization by treatment with papain, by treatment with 3M KCl, and by treatment with detergent. In a preferred method detergent extraction of Class II protein from lymphocytes followed affinity purification is used. Detergent can then be removed by dialysis or selective binding beads, e.g., BIO BEADS (Bio-Rad, Hercules, Calif.)

Figure 1:
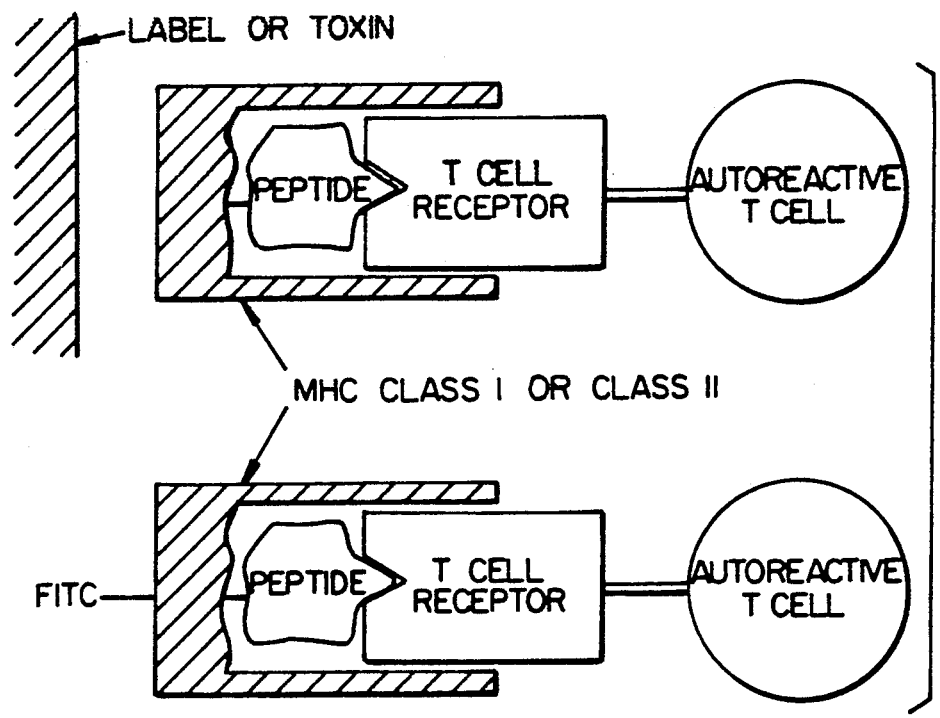
FIG. 1 is a sketch that shows a 3-dimensional structure of the human HLA-A2 antigen (Class I).
Figure 3:
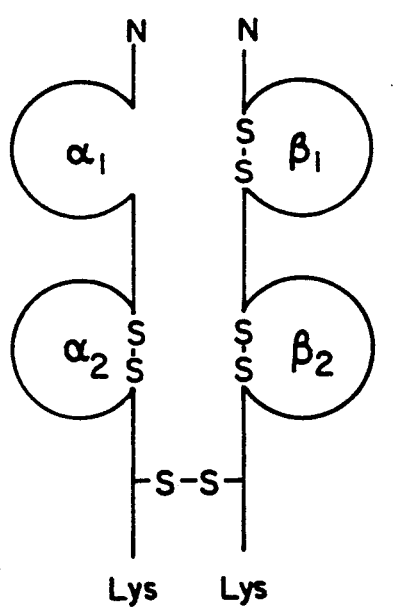
FIG. 3 shows a diagrammatic representation of the active portion of a modified Class II MHC-encoded glycoprotein.

Alternatively, as the amino acid sequence of the murine Class II protein is known, and as the gene has been cloned, the protein can be made using recombinant methods. In a first generation synthetic MHC protein, the heavy (alpha) and light (beta) chains are synthesized using a carboxy terminal truncation which effects the deletion of the hydrophobic domain, and the carboxy termini can be arbitrarily chosen to facilitate the conjugation of toxins or label. For example, in the MHC protein shown in FIG. 3, lysine residues are introduced. In addition, cysteine residues near the carboxy termini are included to provide a means to form disulfide linkage of the chains; the synthetic gene can also include restriction sites to aid in insertion into expression vectors and in manipulating the gene sequence to encode analogs. The alpha and beta chains are then inserted into expression vectors, expressed separately in an appropriate host, such as *E. coli*, yeast, or other suitable cells, and the recombinant proteins obtained are recombined in the presence of the peptide antigen.

Figure 4:
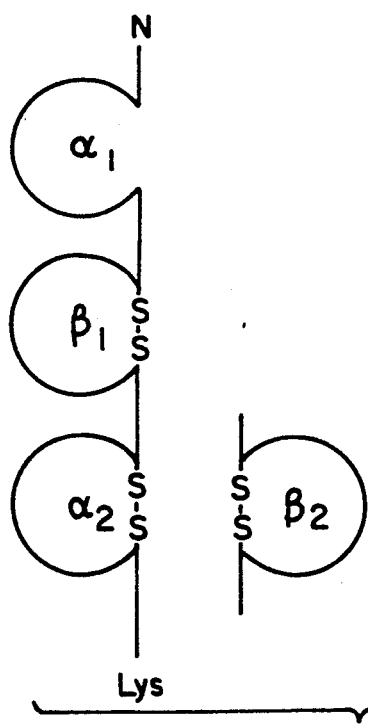
FIG. 4 shows preferred second generation MHC protein designs.
Figure 4:
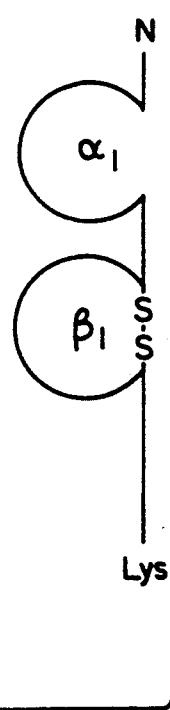

As the availability of the gene permits ready manipulation of the sequence, a second generation preferred construction includes hybrid Class I and Class II features, as illustrated in FIG. 4, wherein the alpha$_1$ and beta$_1$ domains of Class II MHC are linked through a flexible portion that permits intramolecular dimerization between these domains resulting in an edge-to-edge beta sheet contact. The beta$_1$ segment is then fused to the alpha$_2$ domain of Class I with beta$_2$ microglobulin coexpressed to stabilize the complex. The transmembrane and intracellular domains of the Class I gene can also be included but there may be no point in doing so unless liposomes are used to transport the complex. A simpler version includes only the alpha$_1$ and beta$_1$ domains with a C-terminal lysine for toxin conjugation (FIG. 4).

Construction of expression vectors and recombinant production from the appropriate DNA sequences are performed by methods known in the art per se.

Expression can be in procaryotic or eucaryotic systems. Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al, *Gene* (1977) 2:95. Commonly used procaryotic control sequences, which are defined herein to include promoters for transcription initiation, optionally with an operator, along with ribosome binding site sequences, including such commonly used promoters as the beta-lactamase (penicillinase) and lactose (lac) promoter systems (Change et al, *Nature* (1977) 198:1056) and the tryptophan (trp) promoter system (Goeddel et al, *Nucleic Acids Res* (1980) 8:4057) and the lambda-derived P$_L$ promoter and N-gene ribosome binding site (Shimatake et al, *Nature* (1981) 292:128). Any available promoter system compatible with procaryotes can be used.

The expression systems useful in the eucaryotic hosts comprise promoters derived from appropriate eucaryotic genes. A class of promoters useful in yeast, for example, include promoters for synthesis of glycolytic enzymes, including those for 3-phosphoglycerate kinase (Hitzeman, et al, *J Biol Chem* (1980) 255:2073). Other promoters include those from the enolase gene (Holland, M. J., et al *J Biol Chem* (1981) 256:1385) or the Leu2 gene obtained from YEp13 (Broach, J., et al, *Gene* (1978) 8:121).

Suitable mammalian promoters include the early and late promoters from SV40 (Fiers, et al, *Nature* (1978) 273:113) or other viral promoters such as those derived from polyoma, adenovirus II, bovine papilloma virus or avian sarcoma viruses. Suitable viral and mammalian enhancers are cited above.

The expression system is constructed from the foregoing control elements operably linked to the MHC sequences using standard methods, employing standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer or these commercially available restriction enzymes. See, e.g., New England Biolabs, Product Catalog. In general, about 1 ug of plasmid or DNA sequence is cleaved by one unit of enzyme in about 20 ul of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacrylamide gel or agarose gel electrophoresis using standard techniques. A general description of size separation is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 5-10 uM dNTPs. The Klenow fragment fills in a 5' sticky ends but chews back protruding 3' single strands, even though the four dNTPS, are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column.

Synthetic oligonucleotides are prepared using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothretiol, 1-2 mM ATP, 1.7 pmoles $^{32}P$-ATP (2.9 mCi/mmole), 0.1 mM spermidine, 0.1 mM EDTA.

Ligations are performed in 15-30 ul volumes under the following standard conditions and temperatures: 20 mM Tris-HCl pH 7.5, 10 mM $MgCl_2$, 10 mM DTT, 33 ug/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 ug/ml total DNA concentrations (5-100 nM total end concentration). Intermolecular blunt end ligations (usually employing a 10-30 fold molar excess of linkers) are performed at 1 uM total ends concentration.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per ug of vector at 60° C. for about 1 hr. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis can be used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a stand complementary to the phage, an the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand ar sufficient to prevent hybridization. Plaques which hybridize with the probe are then picked, cultured, and the DNA recovered.

In the proteins of the invention, however, a synthetic gene is conveniently employed. The gene design can include restriction sites which permit easy manipulation of the gene to replace coding sequence portions with these encoding analogs.

Correct ligations for plasmid construction can be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmid from the transformants are then prepared according to the method of Clewell, D. B., et al, *Proc Natl Acad Sci USA* (1969) 62:1159, optionally following chloramphenicol amplification (Clewell, D. B., *J Bacteriol* (1972) 110:667). The isolated DNA is analyzed by restriction and/or sequenced by the dideoxy method of Sanger, F., et al, *Proc Natl Acad Sci USA* (1977) 74:5463 as further described by Messing, et al, *Nucleic Acids Res* (1981) 9:309, or by the method of Maxam, et al, *Methods in Enzymology* (1980) 65:499.

The constructed vector is then transformed into a suitable host for production of the protein.

Depending on the host cell used, transformation is done using standard techniques appropriate to such cells. The calcium treatment employing calcium chloride, as described by Cohen, S. N., *Proc Natl Acad Sci USA* (1972) 69:2110, or the RbCl method described in Maniatis, et al, *Molecular Cloning: A Laboratory Manual* (1982) Cold Spring Harbor Press, p. 254 is used for procaryotes or other cells which contain substantial cell wall barriers. For mammalian cells without such cell walls, the calcium phosphate precipitation method of Graham and van der Eb, *Virology* (1978) 52:546 or electroporation is preferred. Transformations into yeast are carried out according to the method of Van Solingen, P., et al, *J Bacter* (1977) 130:946 and Hsiao, C. L., et al, *Proc Natl Acad Sci USA* (1979) 76:3829.

The transformed cells are then cultured under conditions favoring expression of the MHC sequence and the recombinantly produced protein recovered from the culture.

Antigenic Peptides

The antigenic proteins or tissues for a number of autoimmune diseases are known. It is believed that the presentation of antigen by the MHC glycoprotein on the surface of antigen-presenting cells (APCs) occurs subsequent to the hydrolysis of antigenic proteins into smaller peptide units. The location of these smaller segments within the antigenic protein can be determined empirically. These segments are supposed to be 8-15 units in length, and contain both the agretope and the epitope recognized by the T-helper cell. The epitope itself is a contiguous or non-contiguous sequence of 5-6 amino acids which recognizes the antigen-specific receptor of T-helper cells; the agretope is a contiguous or non-contiguous sequence which is responsible for the association of the peptide with the MHC glycoproteins.

The empirical process of determining the relevant 8-15 amino acid subunits is illustrated using the alpha subunit of the acetylcholine receptor of skeletal muscle. In myasthenia gravis (MG) an autoimmune response is directed to a region of this subunit. A loss of the acetyl choline receptors on the postsynaptic membrane of the neuromuscular junction causes the MG symptoms.

In MG autoantibodies against the alpha subunit of the acetylcholine receptor (AChR) are associated with the autoimmune response directed at the AChR. Eighty five percent of MG patients have autoantibodies reactive with the alpha subunit. Of these, 60% have antibodies that bind to a peptide segment of the alpha subunit called the main immunogenic region (MIR) which is located between residues 60 and 80 (Tzartos and Lindstrom, *Proc Natl Acad Sci USA* (1980) 77:755) The peptide segments recognized by autoreactive human T-cells also are located on the alpha subunit (Hohfield, et al, *Proc Natl Acad Sci USA* (1987) The epitopes recognized by these T-cells lie between residues 1-30, 125-147, 169-181, 257-271 and 351-368.

The peptides carrying agretopes permitting presentation of the epitopes associated with alpha subunit of this receptor are determined as follows.

Strains of mice which when immunized with *Torpedo Californicus* AChR, develop a disease with many of the features of human myesthenia gravis are used as a model. MHC Class II glycoproteins are isolated from spleen cells of mice of this strain using lectin and monoclonal antibody affinity supports. The purified MHC Class II proteins are incorporated into phospholipid vesicles by detergent dialysis. The resultant vesicles are then allowed to fuse to clean glass cover slips to produce on each a planar lipid bilayer containing MHC molecules as shown in FIG. 5 (Brian and McConnell, *Proc Natl Acad Sci USA* (1984) 81:6159).

One cover slip containing MHC Class II molecules embedded in the adherent planar lipid membrane is placed in each well of several 24-well culture plates. Each one of the approximately 40 overlapping 20-residue synthetic peptides corresponding to the alpha subunit sequence and containing one or more radiolabeled amino acid residues (prepared as described below) is placed in a well with cover slip and PBS and allowed to incubate several days. The extent of binding of peptide in the MHC Class II glycoprotein "pocket" is measured by the amount of radioactivity incorporated into the MHC Class II-planar lipid membrane on the cover slip versus planar lipid membrane alone. Specific incorporation of radioactivity indicates that the bound peptide contains an agretope (MHC Class II peptide binding site) of one of the several species of MHC Class II molecules present in the planar lipid membrane. In this way, the set of agretopes for the alpha subunit of AChR is defined for the mouse strain that displays the symptoms of MG upon immunization with AChR or purified alpha subunit.

Next, each of the alpha subunit synthetic peptide segments that contain an agretope is again incorporated into the binding "pocket" of isolated MHC Class II proteins embedded in planar lipid membranes on cover slips. One cover slip is added to each well of a 24-well culture plate, and spleen cells from mice immunized against AChR (and from which strain the adherent MHC Class II proteins were isolated) are added to each well. T-cell proliferation, as measured by tritiated thymidine uptake into DNA, indicates that the MHC Class II protein-bound peptide contains both an agretope and an epitope for binding to the T-cell.

The Dupont apparatus and technique for rapid multiple peptide synthesis (RAMPS) is used to synthesize the members of a set of overlapping (10 residue overlap), 20-residue peptides from the alpha subunit of *Torpedo californicus* AChR. The sequence of this peptide is known and is shown in FIG. 6. One or more radioactive amino acids is incorporated into each synthetic peptide. The pentafluorophenyl active esters of side chain-protected, FMOC amino acids are used to synthesize the peptides, applying standard stepwise solid phase peptide synthetic methods, followed by standard side chain deprotection and simultaneous release of the peptide amide from the solid support.

Alternatively the overlapping sequences which include the putative segments of 8-15 amino acids of the antigenic protein, such as acetylcholine receptor protein, can be synthesized on the method of Geysen, H. M., et al *J Immun Meth* (1987) 102:259-274. The synthesized radio labeled peptides are tested by incubating them individually (on the plates) with purified MHC proteins which have been formulated into lipid membrane bilayers as above.

In multiple sclerosis (MS), which results in the destruction of the myelin sheath in the central nervous system, myelin basic protein (MBP), the major protein component of myelin is the principal autoantigen. Pertinent segments of the MBP protein are also determined empirically, using a strain of mice which develops experimental allergic encephalitis (EAG) when immunized with bovine myelin basic protein, the sequence of MBP is shown in FIG. 7.

Systemic lupus erythematosus (SLE) has a complex systemology, but results from an autoimmune response to red blood cells. Peptides which are the antigenic effectors of this disease are found in the proteins on the surface of red blood cells.

Rheumatoid arthritis (RA) is a chronic inflammatory disease resulting from an immune response to proteins found in the synovial fluid.

Insulin-dependent diabetes mellitus (IDDM) results from autoimmune attack on the beta cells within the Islets of Langerhans which are responsible for secretion of insulin. Circulating antibodies to Islets cells surface antigens and to insulin are known to precede IDDM. Critical peptides in eliciting the immune response in IDDM are believed to be portions of the insulin sequence and the Islet's surface proteins.

The relevant antigenic peptide subunits, as they are relatively short, can readily be synthesized using standard automated methods for peptide synthesis. In the alternative, they can be made recombinantly using isolated or synthetic DNA sequences; though this is not the most efficient approach for peptides of this length.

Thus, in summary, a set of labeled test peptides is prepared, and those which bind to MHC in planar lipid membranes containing MHC proteins are shown to contain the agretope.

The identified peptides are then prepared by conventional solid phase synthesis and the subset which contain epitopes for the disease-inducing helper T-cell clones is determined by incubation of the candidate peptides with murine antigen-presenting cells (APC) (or with isolated MHC complex) and spleen or lymph node T-cells from mice immunized with the full length protein. Successful candidates will stimulate T-cell proliferation in this system. This second, smaller, subset represents the suitable peptide component.

The Effector Component

In one embodiment, the complexes of the invention are designed to destroy the immune response to the peptide in question. In this instance, the effector portion of the molecule will be, for example, a toxin, a chemotherapeutic agent, antibodies to cytotoxic T-cell surface molecules, or radioisotopes emitting "hard" e.g., beta radiation. For example, a number of protein toxins are well known in the art including ricin, diphtheria, gelonin, Pseudomonas toxin, and abrin. Chemotherapeutic agents include, for example, doxorubicin, daunorubicin, methotrexate, cytotoxan, and anti-sense RNA. Antibiotics can also be used. Antibodies have been isolated to cytotoxic T-cell surface molecules and these may thus operate as toxins. In addition, radioisotopes such as yttrium-90, phosphorus-32, lead-212, iodine-131, or palladium-109 can be used. The emitted radiation effects the destruction of the target T-cells.

In some cases the active portion of the effector component is entrapped in a delivery system such as a liposome or dextran carrier; in these cases, either the active component or the carrier may be bound in the complex.

If the effector molecule is intended to be a label, a gamma-emitting radioisotope such as technetium-99 or indium-111 can be used. In addition, other types of labeling such as fluorescence labeling by, for example, fluorescein can be used.

The effector component can be attached to the MHC glycoprotein as shown in FIG. 2, or, if its nature is suitable, to the peptide portion. For example, iodine 131 or other radioactive label can often be included in the peptide determinant sequence.

Formation of the Complex

The elements of the complex can be associated by standard means known in the art. For example, protein toxins can be conjugated to the MHC-derived protein by standard dehydration reactions using carbodiimides or by heterobifunctional linkers. The antigenic peptides can be associated noncovalently with the pocket portion of the MHC protein, or they too can be covalently bound.

The sequence of preparing the complex depends on the components in each instance. For example, in a particular protocol, the peptide portion and MHC portion are noncovalently associated by mixing and the effector is then covalently linked, if desired using commercially available linkers, such as SPDP (Pierce Chemicals) to the MHC. Alternatively, the effector and MHC may be first conjugated using a dehydration reaction and the conjugate complexed with the peptide component.

If the effector is itself a protein, the entire complex may be made directly from the appropriate encoding DNA using recombinant methods.

Assessment of the Complex

The complexes of the invention can be assayed using an in vitro system or using an in vivo model. In the in vitro system, the complex is incubated with peripheral blood T-cells from subjects immunized with the protein or antigen responsible for the condition associated with the peptide of the complex. The successful complexes will prevent further proliferation of the antigen specific T-cells even upon stimulation with additional antigen.

In the in vivo system, T-cells that proliferate in response to the isolated epitope or to the full length antigen in the presence of APC are cloned. The clones are injected into histocompatible animals which have not been immunized in order to induce the autoimmune disease. Symptoms related to the disease will then develop. Administration of the relevant complex, including a toxin as effector component, should ameliorate or eliminate the symptoms of the disease.

Administration of a labeled complex permits identification of those portions of the immune system involved in the disease, in diagnostic applications.

Model Systems for In vivo Testing

The following are model systems for autoimmune diseases which can be used to evaluate the effects of the complexes of the invention on these conditions.

1. Systemic Lupus Erythematosus (SLE)

$F_1$ hybrids of autoimmune New Zealand black (NZB) mice and the phenotypically normal New Zealand White (NZW) mouse strain develop severe systemic autoimmune disease, more fulminant than that found in the parental NZB strain. These mice manifest several immune abnormalities, including antibodies to nuclear antigens and subsequent development of a fatal, immune complex-mediated glomerulonephritis with female predominance, remarkably similar to SLE in humans. Knight, et al, *J Exp Med* (1978) 147:1653.

In both the human and murine forms of the disease, a strong association with MHC gene products has been reported. HLA-DR2 and HLA-DR3 individuals are at a higher risk than the general population to develop SLE (Reinertsen, et al, *N Engl J Med* (1978) 299: 515), while in NZB/W $F_1$ mice (H-$2^{d/u}$), a gene linked to the h-$2^u$ haplotype derived from the NZW parent contributes to the development of the lupus-like nephritis.

The effect of the invention complex can be by survival rates and by the process of development of the symptoms, such as proteinuria and appearance of anti-DNA antibodies.

Proteinuria is measured colorimetrically by the use of URISTIK (Miles Laboratories, Inc., Elkhart, Ind.), giving an approximation of proteinuria as follows: trace, 10 mg/dl; 1+, 30 mg/dl; 2+, 100mg/dl; 3+, 300 mg/dl; and 4+, 1000 mg/dl. The development of high grade proteinuria is significantly delayed by treatment of the mice with complex.

The presence of anti-DNA specific antibodies in NZB/W $F_1$ mice is determined by using a modification of a linked immunosorbent assay (ELISA) described by Zouali and Stollar, *J Immunol Methods* (1986) 90:105.

Myasthenia Gravis (MG)

Myasthenia gravis is one of several human autoimmune diseases linked to HLA-D. Safenberg, et al, *Tissue Antigens* (1978) 12:136; McDevitt, et al, *Arth Rheum* (1977) 20:59. In MG antibodies to the acetyl choline receptors (AcChoR) impair neuromuscular transmission by mediating loss of AcChoR in the postsynaptic membrane.

SJL/J female mice are a model system for human MG. In these animals, experimental autoimmune myasthenia gravis (EAMG) is induced by immunizing the mice with soluble AcChoR protein from another species. Susceptibility to EAMG is linked in part to the MHC and has been mapped to the I region within H-2. Christadoss, et al, *J Immunol* (1979) 123:2540.

AcChoR protein is purified from *Torpedo californica* and assayed according to the method of Waldor, et al, *Proc Natl Acad Sci* (USA) (1983) 80:2713, incorporated by reference. Emulsified AcChoR, 15 ug in complete Freund adjuvant, is injected intradermally among six sites on the back, the hind foot pads, and the base of the tail. Animals are reimmunized with this same regimen 4 weeks later.

Evaluation can be made by measurement of anti-AcChoR antibodies. Anti-AcChoR antibody levels are measured by a microtiter ELISA assay as described in Waldor, et al, supra. The standard reagent volume is 50 ul per well. Reagents are usually incubated in the wells for 2 hr at RT. Five ug of AcChoR diluted in bicarbonate buffer, pH 9.6, is added to each well. After incubation with AcChoR, the plates are rinsed four times with a wash solution consisting of phosphate-buffer saline containing 0.05% Tween and 0.05% $NaN_3$. Mouse sera are diluted in 0.01M PBS (pH 7.2), 1.5 mM $MgCl_2$, 2.0 mM 2-mercaptoethanol, 0.05% Tween-80, 0.05% $NaN_3$ (P-Tween buffer) and incubated on the plate. After the plate is washed, beta-galactosidase-conjugated sheep anti-mouse antibody diluted in P-Tween buffer is added to each well. After a final washing, the enzyme substrate, p-nitrophenylgalactopyranoside is added to the plate, and the degree of substrate catalysis is determined from the absorbance at 405 nm after 1 hr.

Anti-AcChoR antibodies are expected to be present in the immunized with AcChoR mice as compared to nonimmunized mice. Treatment with complex is expected to significantly reduce the titer of anti-AcChoR antibodies in the immunized mice.

The effect of treatment with complex on clinical EAMG can also be assessed. Myasthenia symptoms include a characteristic hunched posture with drooping of the head and neck, exaggerated arching of the back, splayed limbs, abnormal walking, and difficulty in righting. Mild symptoms are present after a standard stress test, and should be ameliorated by administration of complex.

Rheumatoid Arthritis (RA)

In humans, susceptibility to rheumatoid arthritis is associated with HLA D/DR. The immune response in mice to native type II collagen has been used to establish an experimental model for arthritis with a number of histological and pathological features resembling human RA. Susceptibility to collagen-induced arthritis (CIA) in mice has been mapped to the H-2 I region, particularly the I-A subregion. Huse, et al, *Fed Proc* (1984) 43:1820.

Mice from a susceptible strain, DBA-1 are caused to have CIA by treatment of the mice with native type II collagen, using the technique described in Wooley and Luthra, *J Immunol* (1985) 134:2366, incorporated herein by reference.

In another model adjuvant arthritis in rats is an experimental model for human arthritis, and a prototype of autoimmune arthritis triggered by bacterial antigens, Holoschitz, et al, *Prospects of Immunology* (CRC Press) (1986); Pearson *Arthritis Rheum* (1964) 7:80. The disease is the result of a cell-mediated immune response, as evidenced by its transmissibility by a clone of T-cells which were reactive against the adjuvant (MT); the target self-antigen in the disease, based upon studies with the same cloned cells, appears to be part(s) of a proteoglycan molecule of cartilage.

Adjuvant disease in rats is produced as described by Pearson, supra, i.e., by a single injection of Freund's adjuvant (killed tubercle bacilli or chemical fractions of it, mineral oil, and an emulsifying agent) given into several depot sites, preferably intracutaneously or into a paw or the base of the tail. The adjuvant is given in the absence of other antigens.

The effect of complex treatment of manifestations of the disease are monitored. These manifestations are histopathological, and include an acute and subacute synovitis with proliferation of synovial lining cells, predominantly a mononuclear infiltration of the articular and particular tissues, the invasion of bone and articular cartilage by connective tissue pannus, and periosteal new bone formation, especially adjacent to affected joints. In severe or chronic cases, destructive changes occur, as do fibrous or bony ankylosis. These histopathological symptoms are expected to appear in control animals at about 12 days after sensitization to the Freund's adjuvant.

Insulin Dependent Diabetes Mellitus (IDDM)

IDDM is observed as a consequence of the selective destruction of insulin-secreting cells within the Islets of Langerhans of the pancreas. Involvement of the immune system in this disease is suggested by morphologic evidence of early infiltration of the Islets by mononuclear cells, by the detection of anti-islet cell antibodies, by the high frequency of HLA-DR3 and -DR4 alleles in IDDM populations, and by clinical associations between IDDM and various autoimmune diseases. An animal model for spontaneous IDDM and thyroiditis has been developed in the BB rat. As in humans, the rat disease is controlled in part by the genes encoding the MHC antigens, is characterized by islet infiltration, and is associated with the presence of anti-islet antibodies. The I-E equivalent Class II MHC antigens appear to be involved in manifestation of the autoimmune diseases in the BB rat. Biotard, et al, *Proc Natl Acad Sci (USA)* (1985) 82:6627.

In morphologic evaluation, insulitis is characterized by the presence of mononuclear inflammatory cells within the islets. Thyroiditis is characterized by focal interstitial lymphocytic infiltrate within the thyroid gland, as a minimum criterion. Most severe cases show diffuse extensive lymphocytic infiltrates, disruption of acini, fibrosis, and focal Hurthle cell change. See Biotard et al supra.

Treatment of the BB rats with complex of the invention is expected to ameliorate or prevent the manifestation of the clinical and morphological symptoms associated with IDDM and thyroiditis.

In another model, the NOD mouse strain ($H-2k^dD^b$) is a murine model for autoimmune IDDM. The disease in these animals is characterized by anti-islet cell antibodies, severe insulitis, and evidence for autoimmune destruction of the beta-cells. Kanazawa, et al, *Diabetologia* (1984) 27:113. The disease can be passively transferred with lymphocytes and prevented by treatment with cyclosporin-A (Ikehara, et al, *Proc Natl Acad Sci (USA)* (1985) 82:7743; Mori, et al, *Diabetologia* (1986) 29:244). Untreated animals develop profound glucose intolerance and ketosis and succumb within weeks of the onset of the disease. Seventy to ninety percent of female and 20-30% of male animals develop diabetes within the first six months of life. Breeding studies have defined at least two genetic loci responsible for disease susceptibility, one of which maps to the MHC. Characterization of NOD Class II antigens at both the serologic and molecular level suggest that the susceptibility to autoimmune disease is linked to $I-A_B$. Acha-Orbea and McDevitt, *Proc Natl Acad Sci (USA)* (1987) 84:235.

Treatment of Female NOD mice with complex is expected to lengthen the time before the onset of diabetes and/or to ameliorate or prevent the disease.

Formulation and Administration

The complexes of the invention are conveniently administered in the form of liposomes or micelles if the transdermal region of the MHC is included. However, if this region is deleted, the complex can be administered in a manner conventionally used for peptide-containing pharmaceuticals. Administration is systemic and is effected by injection, preferably intravenous, thus formulations compatible with the injection route of administration may be used. Suitable formulations are found in *Remington's Pharmaceutical Sciences*, Mack Publishing Company, Philadelphia, Pa., latest edition. A dosage level of 10-500 ug for murine subjects is effective; thus about 0.5 mg/kg to 25 mg/kg is suggested.

The following examples illustrate, but do not limit the invention.

EXAMPLE 1

Preparation of Labeled (I-131) MHCII-BMBP Peptide Complex

An iodinated synthetic peptide representing amino acids 1-13 of bovine myelin-basic protein (BMBP) is synthesized using standard solid phase synthesis for FMOC-protected amino acids. The resulting peptide has the sequence Ac-Ala-Ser-Ala-Gln-Lys-Arg-Pro-Ser-Gln-Arg-Ser-Lys-(I-131)Tyr-NH$_2$. MHCII is purified from spleen cells of PL/J strain mice according to the method of Turkewitz et al (supra) incorporated herein by reference. The purified MHCII in detergent or as a lipid bilayer (supra) is incubated with the synthesized peptide until the radiolabel uptake into the high molecular weight fraction is optimized. The excess radiolabeled peptide is then removed by dialysis or gel filtration and the resulting complex is dialyzed in the presence of lipid to form micelles.

EXAMPLE 2

Use of MHCII-BMBP 131-I as a Toxin

Cloned T-helper cells specific for the N-terminal 13 amino acid sequence of BMBP are obtained from PL/J strain mice immunized with BMBP, by the method of Steinman. The isolated cloned T-helper cells are incubated with the complex prepared in Example 1 at a concentration of $10^6$ cells/ml and 0.1-1.0 ug/ml of the complex for 4-16 hours and 37° C.

The cells are washed and cell survival of the T-lymphocytes is then determined on washed cells. The culture is incubated with concanavalin A and the uptake of tritiated thymidine assessed as an index of T-helper cell survival and proliferation.

The survival of cells after treatment with the radiolabeled complex and in the presence of BMBP and autologous antigen-presenting cells is less than 50% of that of cells incubated with nonlabeled complex or incubated in the presence of tritiated thymidine without BMBP.

What is claimed is:

1. A pharmaceutical composition comprising a pharmaceutically acceptable excipient and an MHC Class II-peptide complex capable of binding a T cell receptor and inducing anergy in a T cell bearing the receptor, the complex consisting essentially of:
   an MHC Class II component comprising extracellular domains of an MHC Class II molecule sufficient to form an antigen binding pocket, said component being encoded by an allele associated with an autoimmune disease, which component is soluble under physiological conditions in the absence of detergent or lipid; and
   an autoantigenic peptide of between about 8 and about 15 amino acids, the autoantigenic peptide being bound to the antigen binding pocket.

2. The composition of claim 1, wherein the autoimmune disease is rheumatoid arthritis.

3. The composition of claim 1, wherein the autoimmune disease is multiple sclerosis.

4. The composition of claim 1, wherein the MHC Class II component is isolated from a spleen cell.

* * * * *